United States Patent [19]
Loseff

[11] 3,993,080
[45] *Nov. 23, 1976

[54] SUCTION TUBE AND RETROGRADE FLUSHING FOR WOUNDS, BODY CAVITIES AND THE LIKE

[76] Inventor: Herbert S. Loseff, 308 Woodley Road, Winnetka, Ill. 60093

[ * ] Notice: The portion of the term of this patent subsequent to Sept. 30, 1992, has been disclaimed.

[22] Filed: July 24, 1975

[21] Appl. No.: 598,890

Related U.S. Application Data

[63] Continuation-in-part of Ser. No. 447,316, March 1, 1974, Pat. No. 3,908,664.

[52] U.S. Cl. .................... 128/350 R; 128/349 B; 128/278
[51] Int. Cl.² .................................... A61M 27/00
[58] Field of Search .................. 128/276–278, 128/349, 350, 335.5, 339

[56] References Cited
UNITED STATES PATENTS

| | | | |
|---|---|---|---|
| 3,125,095 | 3/1964 | Kaufman et al. | 128/335.5 |
| 3,407,817 | 10/1968 | Galleher, Jr. | 128/349 B |
| 3,905,361 | 9/1975 | Hewson et al. | 128/349 B |
| 3,908,664 | 9/1975 | Loseff | 128/350 R |

Primary Examiner—Robert W. Michell
Assistant Examiner—Henry S. Layton
Attorney, Agent, or Firm—Norman Lettvin

[57] ABSTRACT

A drainage tubing for wounds, or body cavities, is described. The tubing is placed and retained in the wound site in an improved manner by means of an inflatable balloon positioned in the intact, healthy tissue adjacent the patient's skin, or in the body cavity adjacent a wall thereof. The drainage tubing may also have a second, collapsible bulb portion for aseptic backflushing of the placement site while the tubing lumen is sealed from the exterior. The specific construction enables a technician to insert the tubing when used in a wound site either from within or without the placement site using an awl to penetrate the exterior tissue adjacent the site.

6 Claims, 2 Drawing Figures

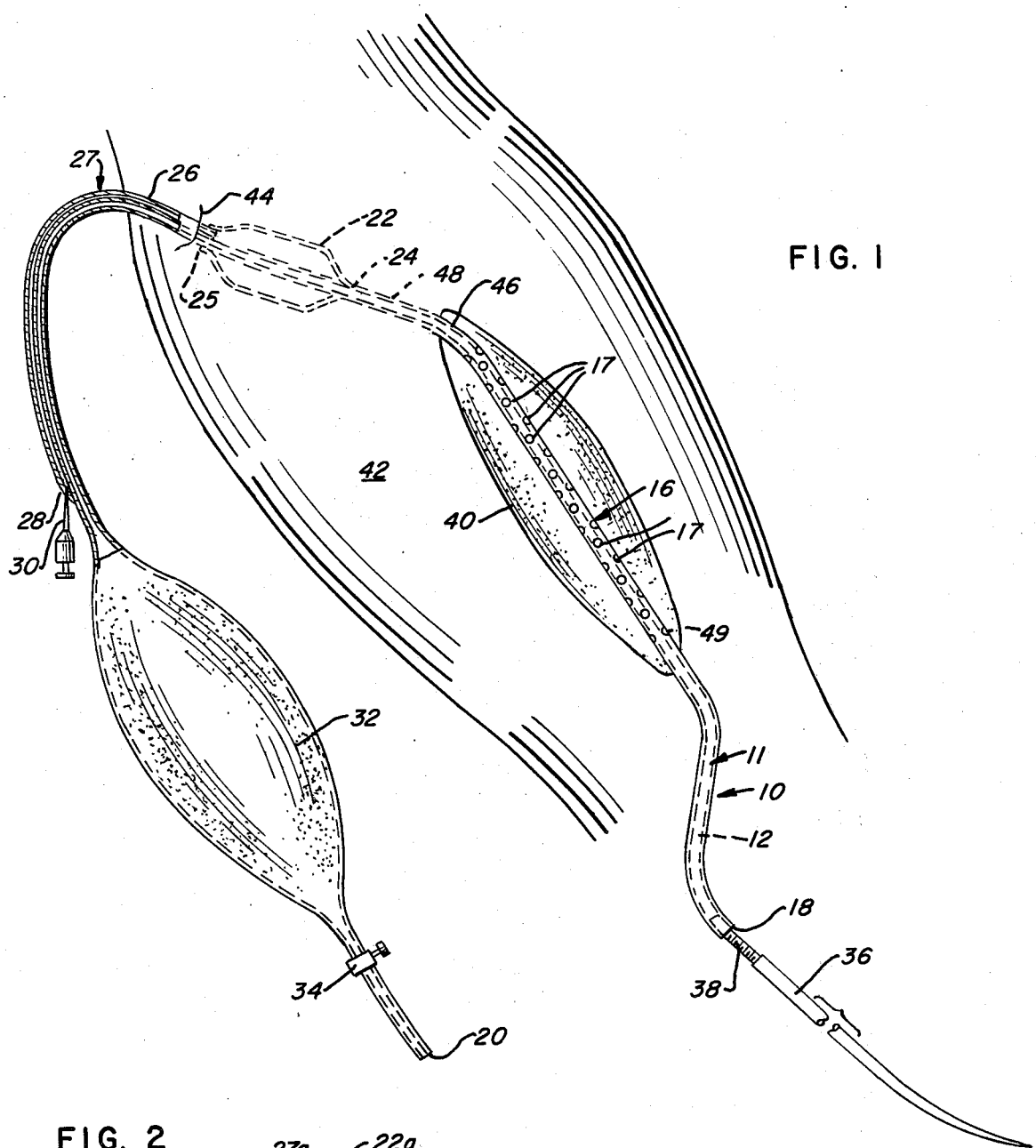

SUCTION TUBE AND RETROGRADE FLUSHING FOR WOUNDS, BODY CAVITIES AND THE LIKE

CROSS REFERENCE TO RELATED APPLICATION

This application is a continuation-in-part of my co-pending application, Ser. No. 447,316 filed Mar. 1, 1974 now U.S. Pat. No. 3,908,664.

BACKGROUND OF THE INVENTION

When a patient has a serious, deep wound, or a large abscess, osteomyelitis, or other collections of body fluids such as serum, blood, or pus in the body, drainage catheter tubing (commonly called wound tubing) is commonly used to alleviate the situation. Commonly, the wound tubing is made of flexible plastic such as polyethylene, or inert elastomers such as silicone rubber or the like. Typically, the wound tubing is fabricated to have sufficient stiffness so that fluids can be removed through it by suction without collapsing the tubing, for example, by an evacuator such as is shown in U.S. Pat. No. 3,115,138.

The wound tubing typically is manufactured with a large number of lateral perforations for communication between the lumen or bore of the tubing and the exterior, the perforations being located in a central portion of the tubing, and the ends of the tubing being free of lateral perforations.

For emplacement in the wound site, a pointed steel awl is connected to one end of the wound tubing, to pass the tubing through healthy, intact tissue adjacent the wound in such a manner that at least one end of the wound tubing is positioned exterior of the patient, while the perforated portion lies at the wound site. Following this, excess portions of the wound tubing, and the awl, are removed by severing the tubing, and the wound site in sutured. In the past, and as disclosed in my co-pending application, Ser. No. 447,316, filed Mar. 1, 1974, the surgeon inserts the wound tubing into the wound by first using an awl to penetrate exterior skin adjacent the wound and then drawing the tubing through the perforation into the wound.

Various significant problems exist in the prior art wound tubing. First, the restless patient can accidentally, or otherwise, pull on the wound tubing and cause it to withdraw outwardly along its path through the healthy tissue. This can happen when the patient is asleep, or irrational patients and children may intentionally try to withdraw the wound tubing.

Once the wound tubing has been partially or completely withdrawn, those portions of the tubing which have been exposed to the exterior will become contaminated with bacteria, and thus should not be simply reinserted into the patient again, even if this were possible. Accordingly, a wound tubing may have to be reinserted by connecting fresh sterile wound tubing to an awl, and once again punching it through the healthy tissue into the wound site. Also, the stitches holding the wound closed may well have to be reopened in order to withdraw the awl and to re-position the wound tubing.

Furthermore, at the skin exit hole or holes of the wound tubing, there is a pronounced tendency for blood, lymph, or irrigation solution to leak outwardly, which is clearly undesirable. Also, there is the still more undesirable possibility of the migration of bacterial contamination inwardly toward the wound site along the wound tubing, and the consequent danger of infection.

Also, the perforations and the bore or lumen of the wound tubing at the wound site frequently become plugged with debris. To avoid changing of the wound tubing, there is frequently attempted a back flushing procedure, in which sterile flushing solution, such as normal saline, is passed through the wound tubing to flush the solution into the wound site. This disperses and breaks up the debris which blocks flow in the wound tubing. This technique has its consequent dangers of introducing bacterial contamination from the exterior into the wound site. The problems present with wound tubing will be recognized by one skilled as being present in tubing lodged in any body cavity, such as in the abdomen, chest, head, neck, or limbs.

In accordance with this invention, the above disadvantages are eliminated or greatly reduced in effect by the improved drainage tubing of this invention and its method of use, and an additional advantage is supplied by providing a construction that more conveniently permits insertion of the wound tubing either from within the wound or cavity site or from without the site as is best for the patient.

BACKGROUND OF THE INVENTION

In accordance with this invention, a drainage device for wounds is provided which comprises a tubular drainage member having a central lumen or bore, and a plurality of drainage ports defined along a first portion of the tubular member and laterally through it for communication between the lumen and the exterior of the tubular member. An elastomeric retention balloon is carried by a second portion of the tubular member at one side of the first portion, which defines the drainage ports. A fill tube of elastomeric material for the retention balloon is provided along a length of the second portion of the tubular member and is normally sealed along its length, but may be pierced by a hypodermic needle or the like to permit pumping in a sufficient amount of air to inflate the retention balloon, after which withdrawal of the needle permits the fine hole left thereby to be sealed by the elastomeric character of the material of the fill tube. The balloon is positioned to be inflatable under sound tissue, such as under the skin of a patient, while the drainage ports lie in the wound or cavity site. Preferably, the first portion of the tubular member described above is spaced from the ends of the tubular member by a convenient length of port-free tubing to permit connection of the tubular member with an awl, for installation of the tubular device in a manner described below, as well as to provide other flexibility of use of the wound tubing of this invention.

It is also a feature of this invention to provide an enlarged lumen, either attachable to or as an integral portion on the tubular drainage member, for use as a collapsible squeeze bulb and storage portion, for retention of flushing solution in the tubular member outside of the body when the drainage device is positioned in a patient with the drainage ports located in the wound or body cavity site. With this arrangement, the lumen or bore of the tubular member can be sealed from the exterior by appropriate clamp means after filling with flushing solution, and the enlarged lumen portion of the tubular member can be squeezed and manipulated for aseptic back flushing of the drainage device, while the tubular member is sealed against possible bacterial contamination from the outside. Accordingly, the wound site can be bathed or back-flushed with any desired solution in a manner which reduces the risk of contaminating the wound site. In the preferred form of this invention the fill tube extends from the retention balloon and terminates adjacent to but short of the enlarged lumen, whether the enlarged lumen is integral with or attachable to the tubular drainage member.

Another preferred feature of this invention is that the drainage ports are of smaller aperture size than the diameter of the central lumen of the tubular drainage member. As a result of this, the drainage ports serve to screen out tissue particles, small blood clots, and the like, preventing them from entering the central lumen and causing obstruction within the tubular drainage member.

It is generally desirable for the tubular drainage member and balloon member of the device of this invention to be made of silicone rubber, since such material is highly non-adherent to clots and debris, and is thus easily flushed. Also, very little tissue reaction occurs in tissue which is in prolonged contact with silicone rubber. Accordingly, the patient may experience considerably increased comfort when a silicone rubber drainage device is used in accordance with this invention.

If desired, organic plastic or rubber drainage devices made in accordance with this invention can be fabricated with a coating of room temperature vulcanizing silicone rubber or the like for essentially equivalent effect.

Other hydrophobic, flexible thermoplastic materials, such as polyethylene, can also be used with advantage to fabricate the devices of this invention. Other corresponding medical grade materials such as latex rubber and polyvinylchloride plastisol can also be used.

The drainage device of this invention is used to provide the drainage to a wound site or the like in a patient by inserting the tubular drainage member into the wound site in such a position that the lateral drainage ports are in flow communication with the wound site. Also, the tubular member is passed through healthy, intact tissue adjacent the wound site so that one end of the tubular member is exposed to and communicates with the exterior of the patient, and in such manner that the balloon retention member is positioned within the healthy, intact tissue adjacent the skin. Generally, either of the above steps may be performed first with equivalent effect.

After the tubular drainage member has been properly emplaced, the balloon member is inflated, to firmly retain the drainage member in the wound site, so that it is less likely to be accidentally or otherwise removed from proper emplacement by pulling on an exposed portion of the tubular member. Likewise, the pressurized balloon member provides an improved seal at and just below the skin level, which greatly reduces or eliminates bleeding and fluid leakage from the skin hole through which the tubular member passes. The balloon inflation also reduces the possibility that bacterial contamination can enter the skin hole to cause infection.

Other advantages of this invention will be readily apparent from the specific embodiments of this invention described below.

In the drawings:

FIG. 1 is an illustrative view, with some portions broken away, showing use of one form of drainage device or wound tubing, and illustrating the emplacement of the wound tubing by drawing it into the wound from without the wound;

FIG. 2 is fragmentary view showing another form of device wherein the wound tubing may be emplaced by being drawn into position from within the wound, after which an enlarged lumen may be connected thereto to serve the same function as the enlarged lumen shown in FIG. 1.

Referring to the drawings, FIG. 1 shows a drainage member or wound tubing 10 which comprises a tubular member 11 of flexible, plastic tubing such as silicone rubber, polyethylene, or medical grade polyvinyl chloride plastisol, which is typically about 2 or 3 feet in length. The tubing has a lumen or bore 12 which may be about ⅛ inch in diameter or other diameters as required. The tubing has a lead in end 18 and the other end is at 20.

A first, intermediate portion 16 of tubing 11 defines a plurality of lateral drainage ports in the wall of tubing 11 for fluid communication between lumen 12 and the exterior of tubular member 11. The portion 16 of the tube is preferably spaced from the end 18 thereof, by a convenient length of say at least 3 inches, and preferably about 6 to 8 inches of port-free tubing for purposes which will become apparent below.

A retention balloon 22 is positioned at one side of the drainage ports defined in first portion 16 of tubular member 11. Balloon 22 is generally positioned so that it can be inflatable under the skin of a patient when the drainage ports lie in a wound site. Balloon 22 may be fabricated in a conventional manner by appropriately glueing or otherwise sealing an elastomeric sleeve at regions 24 and 25 to the tubing 11. The balloon 22 has an elongated extension portion 26 sealed along its length to the exterior wall of tube 11 and defining either within itself or with the exterior of tube 11 a second tubular fill passageway or lumen 27 for balloon 22. The balloon 22 may be inflated by passing saline solution, air, or the like through the fill passageway, or tube, 27 which is carried along a portion of the length of tubing 11. Fill tube 27 is of relatively small dimension and does not appreciably enlarge the total diameter of the combined tube 11 and fill tube 27. The distal end 28 of extension portion 26 is sealed to tube 11, but is, pierceable, as is well known in the art, by a hypodermic needle 30 or the like for purposes of pumping through tube 27 air or liquid for purposes of inflating balloon 22. Balloon 22 is preferably made of an elastomer such as silicone rubber, or alternatively, natural latex.

A distal portion of tubing 11 beyond the distal end 28 of fill tube 27 and spaced therefrom forms an enlarged lumen portion 32, which may be used as collapsible squeeze bulb, as well as a storage portion for retention of a flushing solution (such as physiological saline, containing an antibiotic) in a position outside of the body when the wound tubing is positioned in a patient. The end portion 20 of tubing 11 may be sealed by a conventional screw clamp 34, or the like that slips over the end 20, so that the entire lumen 12 of the wound tubing may be filled with flushing solution, including enlarged lumen portion 32, and then the clamp 34 may be closed to seal the lumen from communiction with the exterior.

FIG. 1 shows one technique for emplacement of the wound tubing of this invention in a wound. It should be noted that, for purposes of this invention, the term "wound" is also intended to include other areas of use of the device of this invention as mentioned above, such as body cavities, abscesses, and other sites for accumulations of body fluid.

As shown in FIG. 1, a conventional awl 36 having a threaded connector member 38, of appropriate size, is threaded into end 18 of the wound tubing. The wound tubing can then be emplaced in an open wound 40 on the body portion 42 of a patient. The surgeon penetrates the skin, or tissue, at a point 44 spaced from wound 40, to pass the awl through intact, healthy tissue, manipulating the awl so that it enters the wound site at a point 46. Tubing 11 can then be drawn through the punctured path 48 through the intact, healthy tissue until the portion 16 of the tubing defining the drainage ports 17 lies in the wound site and balloon member 22 has entered skin opening 44. Some surgeons may prefer to allow a portion of balloon member 22 to remain outside of skin opening 44. Also, for best sealing, it is generally preferable for balloon member 22 to reside in essential contact with skin opening 44 and not to be significantly spaced therefrom.

Following this, section 16 of the tubing is positioned as desired by the surgeon in the wound 40, and tubing 11 is severed at a location indicated generally at 49, in accordance with the discretion of the surgeon, so that the awl 36 and usually most of the port-free end portion 18 of the tubing can be removed. Accordingly, first tubing portion 16 is positioned, without the need to handle or touch it, since manipulations of the tubing for mounting and using the awl 36 can be confined to imperforate end 18 of the tubing. Accordingly, section 16 of tubing 11 can more likely remain in aseptic condition. The wound 40 may then be sutured, with drainage port-defining portion 16 of tubing 11 remaining positioned within the wound site.

At the discretion of the surgeon, when he believes the wound tubing to be satisfactorily positioned, balloon 22 can be inflated, typically by pumping in through fill tube 27 physiological saline solution, gas or air by means of a hypodermic needle 28 to which may be connected a conventional syringe or pump, to inflate balloon 22 to the degree desired, to provide firm anchoring of wound tubing 11 coupled with sealing of puncture site 44 in the skin.

Enlarged lumen portion 32 can be collapsed, generally by hand, to force flushing solution through drainage ports 17, as well as the severed end of tubing 11 within wound site 40, to flush the wound tubing in an aseptic manner as desired by the physician.

If the wound site is not open to the exterior, then the surgeon must use the awl to define another exit path through intact tissue in order to position the wound tubing properly. In this event, both ends of the wound tubing protrude from the patient, and can be used for drainage and flushing, but the retention and sealing of one end is still provided by balloon 22. For such special use, a second balloon could be provided for sealing and retaining the second end of the wound tubing.

Optionally, clamp 34 can be opened to replace the flushing solution, or to subject the wound site with an alternating suction-irrigation treatment with antibiotics and other medicinals, for bathing the wound continuously with therapeutic agents.

FIG. 2 shows an alternative embodiment of the wound tubing of this invention, which comprises a similar tubular drainage member 11a which defines a plurality of drainage ports 17a defined through a first portion 16a of the tubular member which is spaced from th ends thereof in a manner similar to the embodiment of FIG. 1. A similar balloon sleeve 22a is also provided, with an inflation or fill tube 27a. In this form the elongated wall portion 26a that seals to the outer wall of tube member 11a to define fill tube 27a is shown separate from but sealed to balloon 22a and providing a pierceable end wall 28a. It is contemplated that adjacent tubes 27a and 11a having a common wall therebetween might be formed by an extrusion and then sealed where desirable to provide a confined fill tube that communicates only with balloon 22. The material of the wall of tubular fill means 27a is collapsible under lateral pressure, and the cross-section of fill means 27a is small relative to the cross-section of tubular member 11a.

It will be noted that, in this embodiment, a tubular portion 50, which is separate from tubing 11a is provided. Tubular portion 50 has an enlarged collapsible lumen portion 52, and a connector means 54 for connection in aseptic, leakproof manner with an end 19 of tubing 11a when desired. The collapsible lumen 52 has a nipple end 20a that may slidably receive thereonto a clamp 34a. Connector 54 may be a hollow tubular member with threads on the outside, proportioned to screw into the lumen of tube 11a for connection therewith. Connector 54 may also be a simple nipple or luer for liquid tight fit into the lumen or bore of tubing 11a.

An advantage of the embodiment of FIG. 2 is that it may be either emplaced in a wound 40 in the manner described above with respect to FIG. 1, or may be emplaced in the wound in reverse manner. An awl may be emplaced in the bore of the opposite end 19 of tube 11a, when compared with the emplacement of the awl as shown in FIG. 3, so that the awl may enter the intact, healthy tissue at point 46 and pass through the tissue until it exits at point 44, should the surgeon find it desirable to do so. The relatively small cross-sectional size of the additional fill tube 26a – 27a compared to the cross-section of the tubular member 11a, and its collapsible nature readily permits such an operation. Tubing 11a can then be positioned in a manner comparable to that shown in FIG. 1 and the awl may be removed. Then, tubular portion 50 may, if desired, be aseptically connected to end 19, and the wound tubing arrangement used in the manner previously described. The ends of tubular member 11a extending beyond the tubular fill means and the perforate first portion 16a permit selective connection to one or the other, as desired, without contaminating the drainage ports or damaging the tubular inflating means.

If desired, tubing 11 or 11a may be connected at its respective end 20 or 20a to a parenteral solution container which is hung above the arrangement, to provide a supply of pressurized flushing solution as desired. Clamp 34, 34a can be used to control the access of such solution to the tubing 11, 11a.

When it is determined that the wound tubing should be removed, balloon 22, 22a may be deflated through withdrawal of the inflating gas or fluid by use of a hypodermic or merely by rupturing fill tube 27, 27a. Tubing 11, 11a can then simply be withdrawn through skin hole 44 without opening of the stitches of wound 40.

While in the preferred use of the invention, the balloon 22 is positioned to be inflatable in the patient's flesh under the skin, if the doctor feels that it is desirable or advisable, the balloon may also be located anywhere along the length of the puncture path 48 made by the awl, or even within the wound itself, and be inflated therein.

It is contemplated that two (or more) of the drainage devices of this invention may be simultaneously emplaced in a wound site. Accordingly, one of the drainage devices may be used as a flushing fluid inlet, while the other drainage device serves as an outlet for the fluid and other drainage. Also, while the drainage portions 16 and 16a of the tube have been disclosed as perforate, it will be understood that other drainage terminal constructions could be used and attached to a perforate or imperforate drainage tube after emplacement, such as by use of Y or T connections between other drain tube sections and the main drainage tube.

What is claimed is:

1. In a drainage device for wounds, body cavities, and the like, said device comprising an elongated tubular drainage member having a central lumen, and a plurality of drainage ports defined along a first portion of the length of said tubular member and through said tubular member for fluid communication between said lumen and the exterior of said tubular member, the improvement comprising, in combination, an elastomeric retention balloon carried by a second portion of said tubular member located to one side of one end of the first portion, and adapted to be inflatable under the skin of a patient when said first portion is properly positioned in a wound, said tubular member also carrying means for inflating and deflating said retention balloon, a length of severable imperforate tubing extending from the end of said first portion and having a terminus adapted for screw connection to an awl, said imperforate length of tubing permitting selective connection to an awl without contamination of the drainage ports in said first portion, an enlarged-lumen portion in communication through the central lumen with the drainage ports and for use as a combination squeeze pump and storage portion for retention of a flushing solution therein, means for selectively sealing said enlarged-lumen portion so that squeezing said squeeze pump operates to back flush solution through the drainage ports, and the means for inflating and deflating the retention balloon being a second tube that is secured along its length to said tubular member and extends along said tubular member from said retention balloon toward said enlarged-lumen but terminating spaced from said enlarged-lumen.

2. The drainage device of claim 1 wherein the cross-section size of the second tube is smaller than that of the tubular member, the tubular member being separate from the enlarged-lumen, and each end of the tubular member permitting selective connection to an awl, thereby permitting the tubular member to be drawn by such an awl from either end through tissue into the drainage site.

3. The drainage device of claim 1 wherein the wall of the second tube is of a pierceable but self-sealing material capable of maintaining fluid pressure developed within the tubular means and the retention balloon.

4. The drainage device of claim 1 wherein the enlarged-lumen portion is formed integral with an end of the tubular member that is spaced from the second tube.

5. In a drainage device for wounds, body cavities and the like, said device comprising an elongated tubular drainage member having a central lumen, drainage means defined along a first portion of the length of said tubular member through the wall of said tubular member for fluid communication between said lumen and the exterior of said tubular member, the improvement comprising, in combination, an elastomeric retention balloon carried by a second portion of said tubular member adjacent one end of the first portion of said tubular member, an elongated second tubular means secured along its entire length to a portion of the length of the tubular member and extending from the retention balloon in a direction away from said first portion of the tubular member, the opposite ends of the tubular member extending respectively beyond the drainage means in the first perforate portion and the tubular means carrying portion, the cross-section size of the second tubular means being smaller than that of the tubular member, and each end of the tubular member permitting selective connection to an awl without contamination of either the drainage ports or damage to the tubular means, thereby permitting the tubular member, with second tubular means secured thereto, to be drawn by such an awl from either end through tissue into the drainage site.

6. The method of providing drainage from a wound site or the like in a patient which comprises:
   inserting a tubular drainage member, having a plurality of lateral drainage ports defined along a first portion of said tubular drainage member, into the wound site in a position such that said drainage ports are in flow communication with said wound site,
   using a pointed penetrating means that is removably secured to an end of said drainage member for passing a second portion of said tubular member through intact, healthy tissue so that one end of said tubular member communicates with the exterior,
   positioning a balloon retention member carried by said second portion of the tubular member within the intact, healthy tissue adjacent the patient's skin at the same time that the tubular drainage member is being positioned in the wound site; and
   inflating the balloon member, to firmly retain the tubular member in the wound site, and to seal the area between said tubular member and said intact, healthy tissue.

* * * * *